US010870846B2

(12) United States Patent
Scott et al.

(10) Patent No.: US 10,870,846 B2
(45) Date of Patent: Dec. 22, 2020

(54) CELLULAR HIGH THROUGHPUT ENCAPSULATION FOR SCREENING OR SELECTION

(71) Applicant: Universität Zürich, Zürich (CH)

(72) Inventors: Daniel Scott, Brunswick West (AU); Andreas Plückthun, Zürich (CH)

(73) Assignee: Universität Zürich, Zürich (CH)

( * ) Notice: Subject to any disclaimer, the term of this patent is extended or adjusted under 35 U.S.C. 154(b) by 505 days.

(21) Appl. No.: 14/371,031

(22) PCT Filed: Jan. 9, 2013

(86) PCT No.: PCT/EP2013/050330
§ 371 (c)(1),
(2) Date: Jul. 8, 2014

(87) PCT Pub. No.: WO2013/104686
PCT Pub. Date: Jul. 18, 2013

(65) Prior Publication Data
US 2015/0031549 A1 Jan. 29, 2015

(30) Foreign Application Priority Data
Jan. 9, 2012 (EP) .................................... 12150453

(51) Int. Cl.
C40B 30/04 (2006.01)
C12N 15/10 (2006.01)
(52) U.S. Cl.
CPC ..... C12N 15/1037 (2013.01); C12N 15/1058 (2013.01); C12N 15/1068 (2013.01); C40B 30/04 (2013.01)

(58) Field of Classification Search
None
See application file for complete search history.

(56) References Cited

U.S. PATENT DOCUMENTS

2004/0241759 A1* 12/2004 Tozer ................... B01J 19/0046
506/4

FOREIGN PATENT DOCUMENTS

| WO | 1993/03151 | 2/1993 |
| WO | 2009/101383 | 8/2009 |
| WO | 2011/047870 | 4/2011 |

OTHER PUBLICATIONS

Hardeman et al. (2006) "Metagenomic approach for the isolation of a novel low-temperature-active lipase from uncultured bacteria of marine sediment" FEMS Microbiology Ecology 59(2):524-534.*
(Continued)

Primary Examiner — Christian C Boesen
(74) Attorney, Agent, or Firm — Wolf, Greenfield & Sacks, P.C.

(57) ABSTRACT

The invention relates to a method for selecting a sequence set from a library of expressed nucleic acid sequences, wherein cells are provided, each cell comprises an expressed nucleic acid sequence expressed as a target protein. The cells are encapsulated by treating them with a cationic polysaccharide and subsequently treating them with an anionic polysaccharide, yielding encapsulated cells, perforating the membrane of the encapsulated cells, yielding solubilized compartments, contacting them with a ligand to said target protein, the ligand bearing a detectable label, and selecting a subset of solubilized compartments as a function of detectable label and isolating the expressed nucleic acid sequences from the selection as a selected sequence set.

15 Claims, 14 Drawing Sheets

(56) References Cited

OTHER PUBLICATIONS

AMS Biotechnology "Gentle Cell Lysis with Higher Yield of Native Proteins" obtained from http://www.amsbio.com/brochures/Solulyse, created Jun. 6, 2006, modified Mar. 16, 2010.*
Biology Online Biology Dictionary; https://www.biology-online.org/dictionary/Constitutive_expression; accessed Nov. 9, 2019.*
Hillberg et al., "Biorecognition through Layer-by-Layer Polyelectrolyte Assembly: In-Situ Hybridization on Living Cells", Biomacromolecules 2006, 7, 2742-2750, XP-002621749, American Chemical Society.
Dodevski et al., "Evolution of Three Human GPCRs for Higher Expression and Stability", Journal of Molecular Biology, 2011, 408, 599-615, XP-28209045, Elsevier Ltd.
Sarkar et al., "Directed Evolution of a G Protein-Coupled Receptor for Expression, Stability, and Binding Selectivity", PNAS, vol. 105, No. 39, Sep. 30, 2008, 14808-14813, XP-002676366, The National Academy of Sciences of the USA.
Sarkar et al., "Supporting Information" (of document listed above at No. 3), PNAS, 10.1073/pnas.0803103105, XP-002676367.
Dalby et al., "Strategy and Success for the Directed Evolution of Enzymes", Current Opinion in Structural Biology 2011, 21: 473-480, Science Direct, XP-002676368.
Miyazaki et al., "Exploring Nonnatural Evolutionary Pathways by Saturation Mutagenesis: Rapid Improvement of Protein Function", Journal of Molecular Evolution, 49: 716-720, 1999, XP-002676369.
Chen et al., "Tuning the Activity of an Enzyme for Unusual Environments: Sequential Random Mutagenesis of Subtilisin E for Catalysis in Demethylformamide", Proc. Natl. Acad. Sci. USA, vol. 90, pp. 5618-5622, Jun. 1993, Biochemistry, XP-002676370.
Krol et al., "Encapsulated Living Cells on Microstructure Surfaces", Langmuir 2005, 21, 705-709, Sep. 2004, American Chemical Society, XP-002696260.
Diaspro et al., "Single Living Cell Encapsulation in Nano-organized Polyelectrolyte Shells", Langmuir 2002, 18, 5047-5050, Feb. 2002, XP-002621748.
Stemmer, "Rapid Evolution of a Protein In Vitro by DNA Shuffling", Nature, vol. 370, Aug. 1994, XP-002082182.
Zhou et al., "Building a Thermostable Membrane Protein", The Journal of Biological Chemistry, vol. 275, No. 10, Mar. 10, 2000, pp. 6975-6979, XP-002380726.
Tate et al., "Engineering G Protein-Coupled Receptors to Facilitate their Structure Determination", Current Opinion in Structural Biology 2009, 19: 386-395, Aug. 2009, Elsevier Ltd.
Scott et al., "Direct Molecular Evolution of Detergent-Stable G Protein-Coupled Receptor Using Polymer Encapsulated Cells", Journal of Molecular Biology (2013) 425; pp. 662-677, Sep. 2012, XP-002696261.

* cited by examiner

Fig. 2b/2c
b
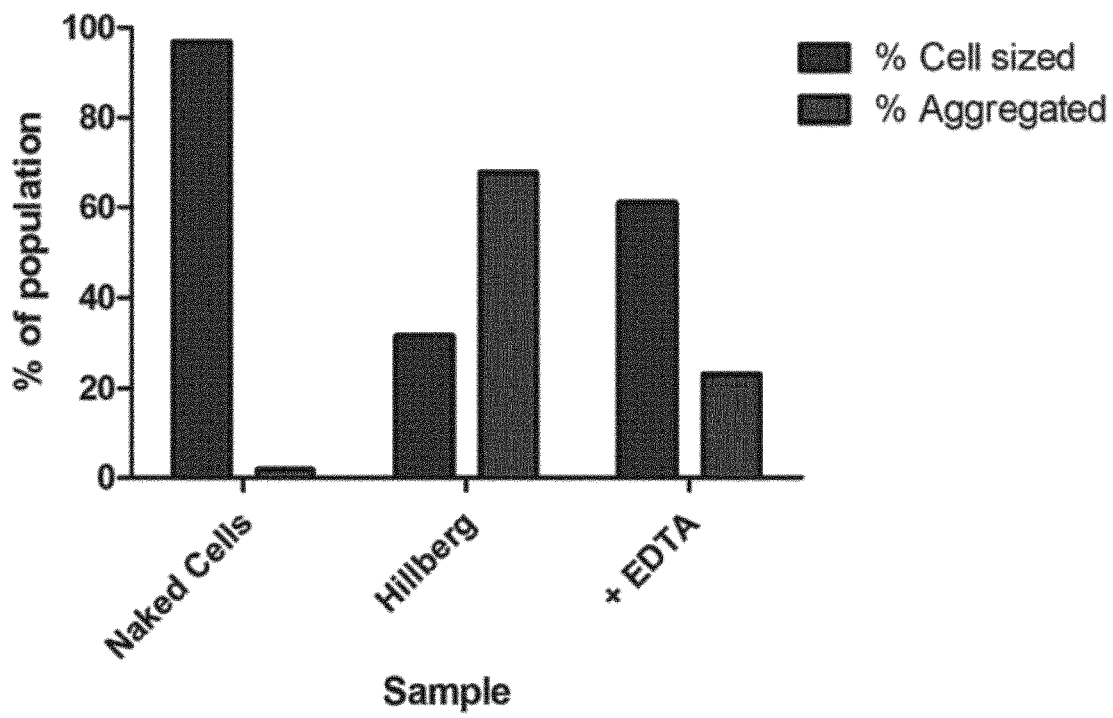
b
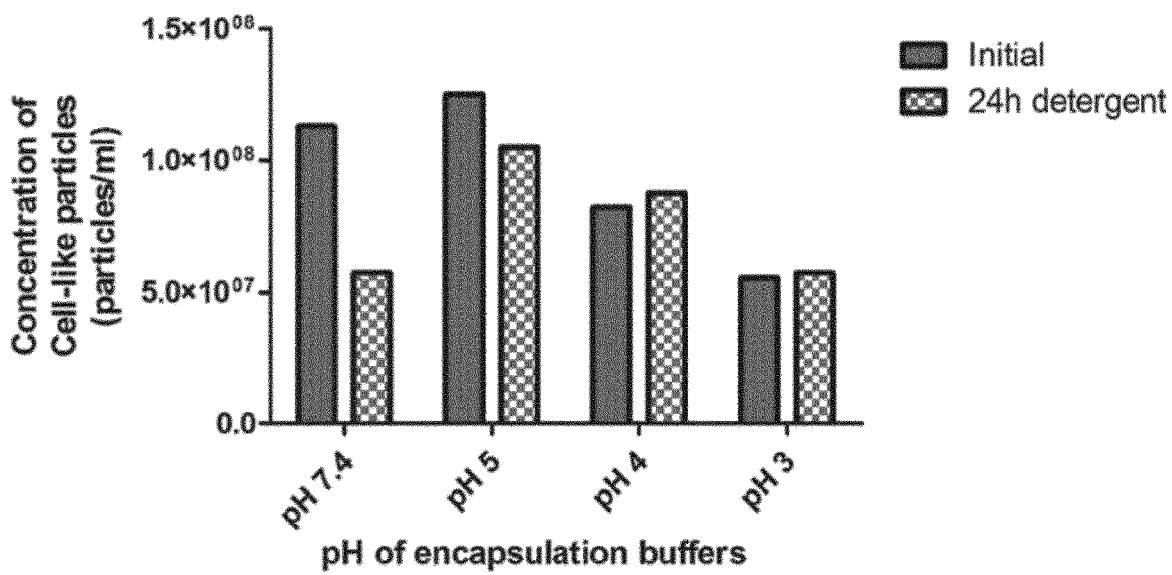
c a  b c

Figure 3:
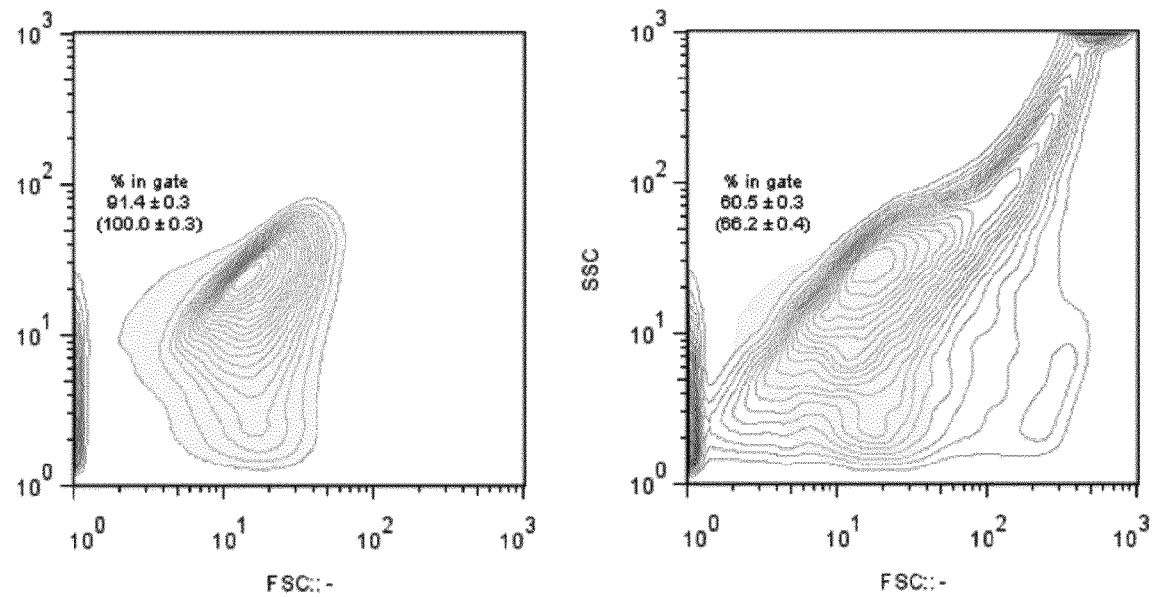
Figure 3:
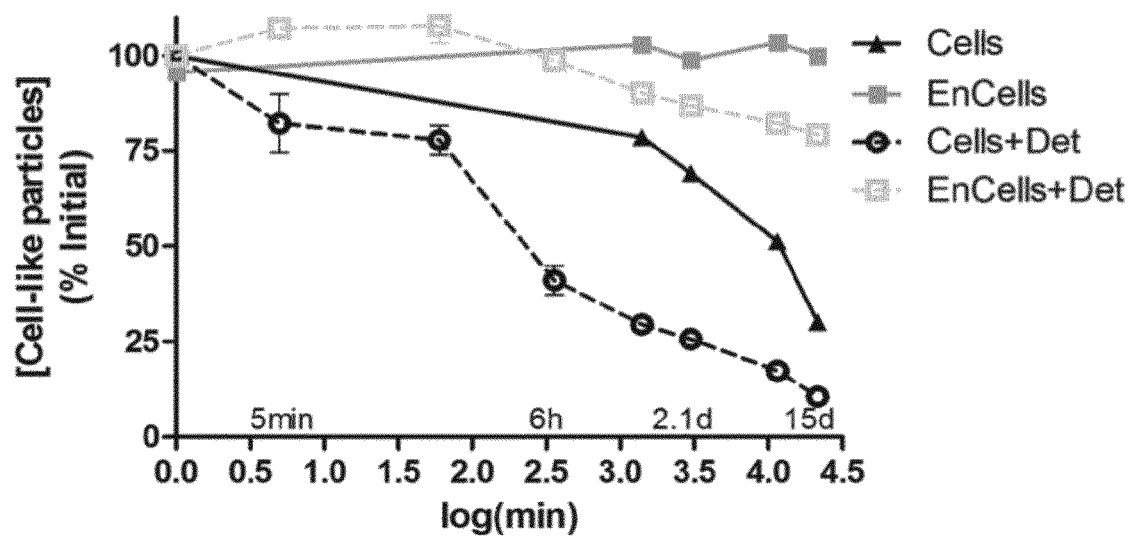

Fig. 3 d, e
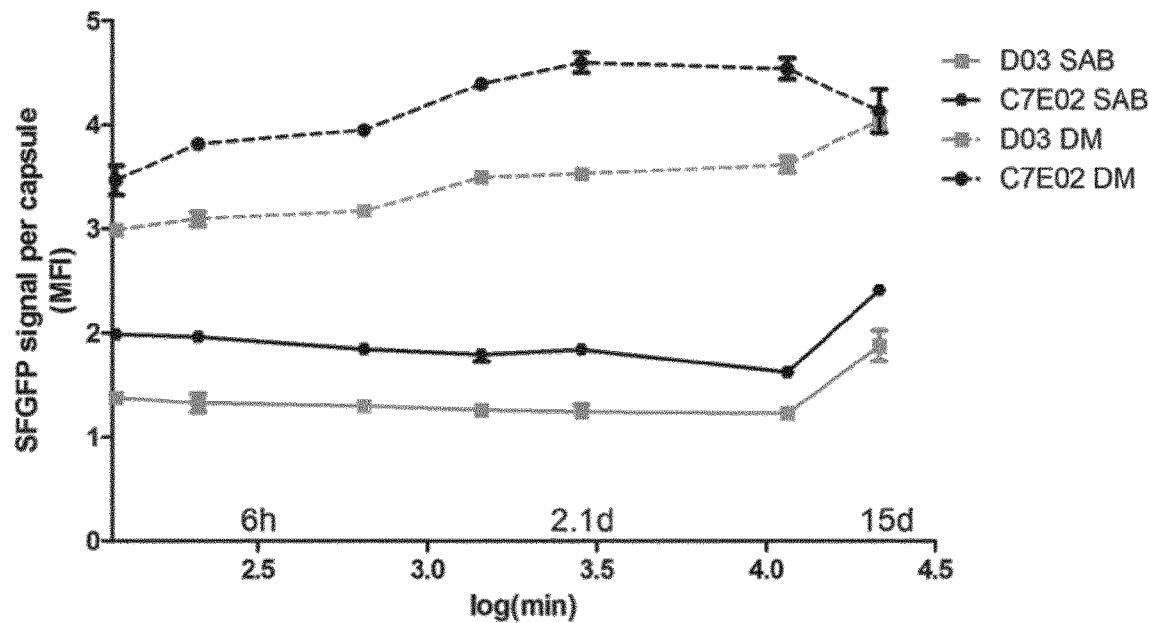
d
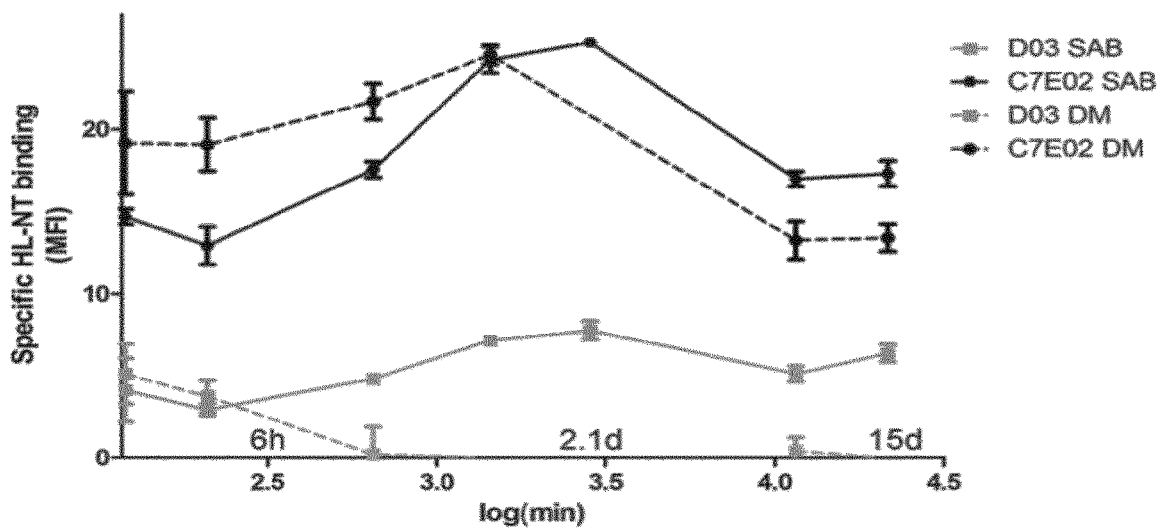
e a b

Figure 5:
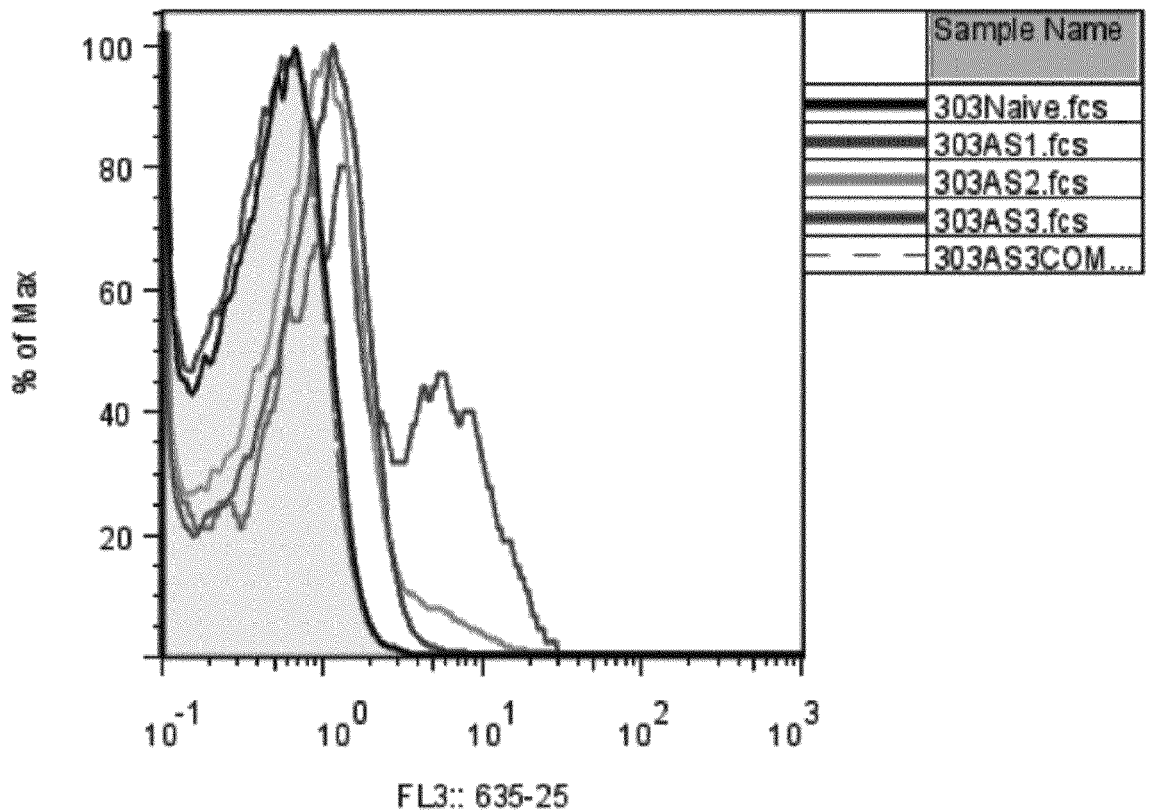
Figure 5:
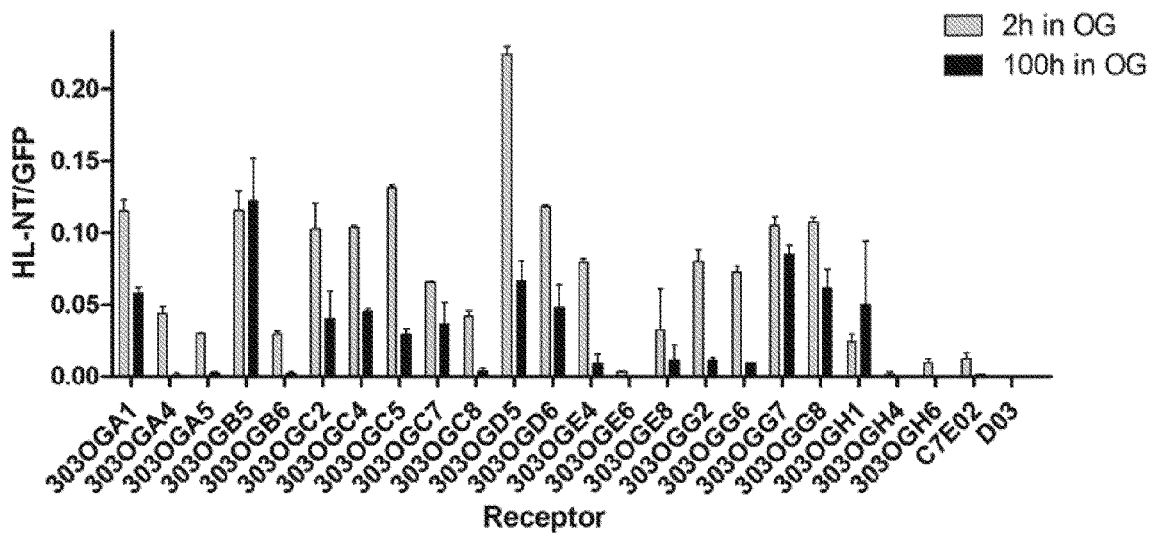

Fig. 5 c-d
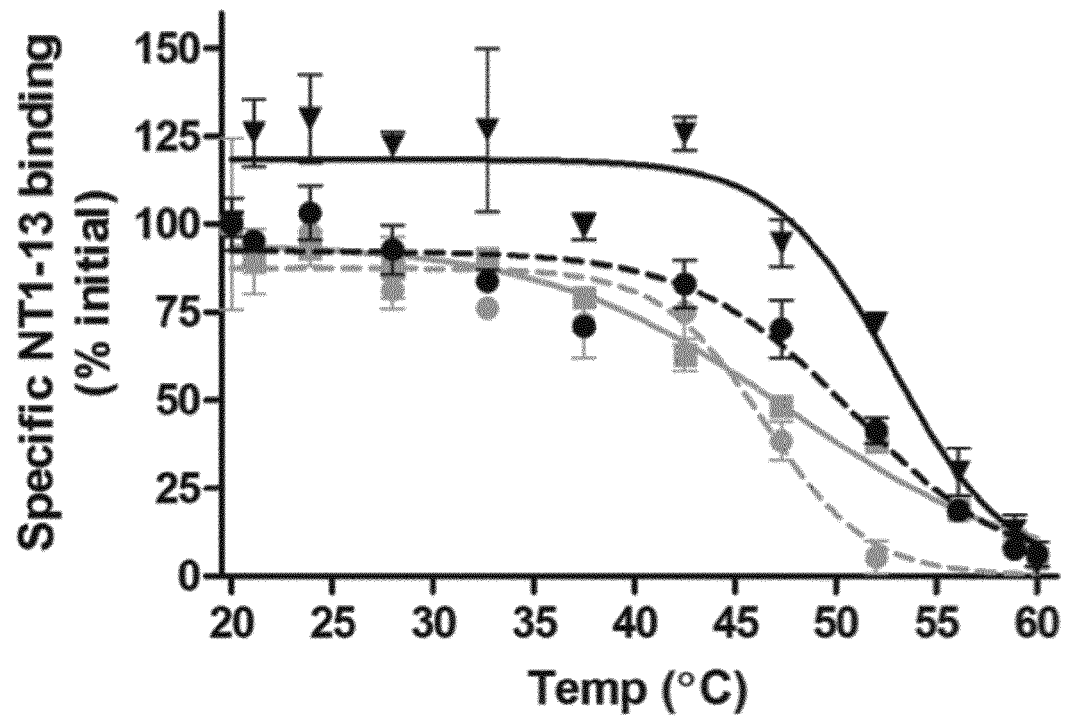
c
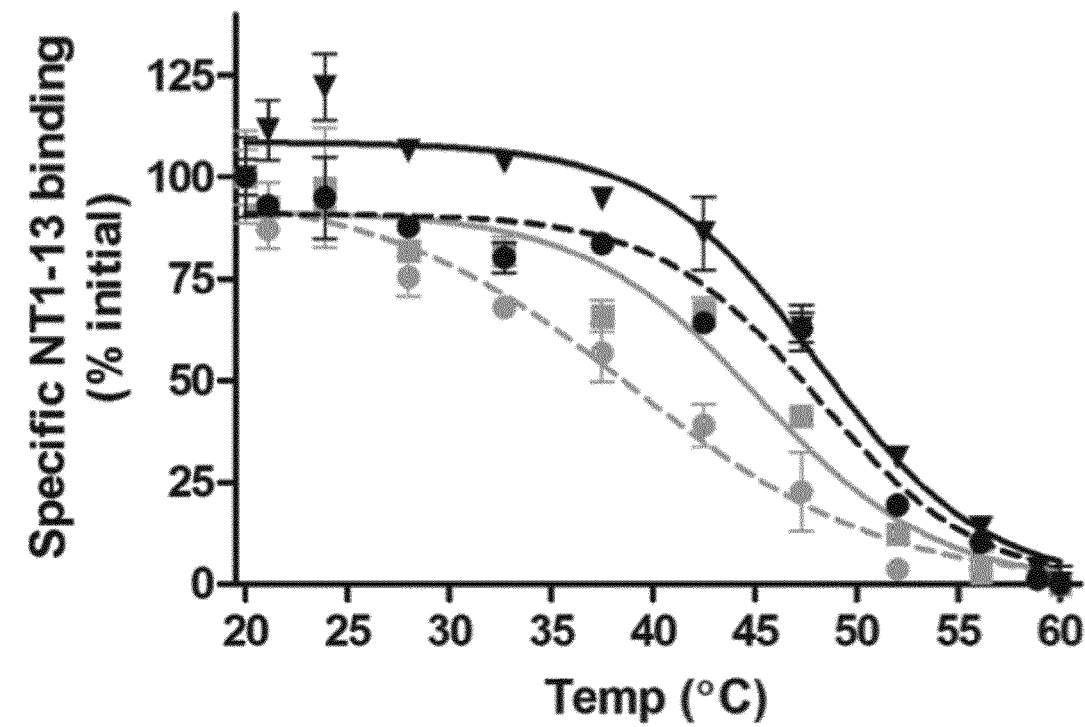
d

Fig. 5 e-f
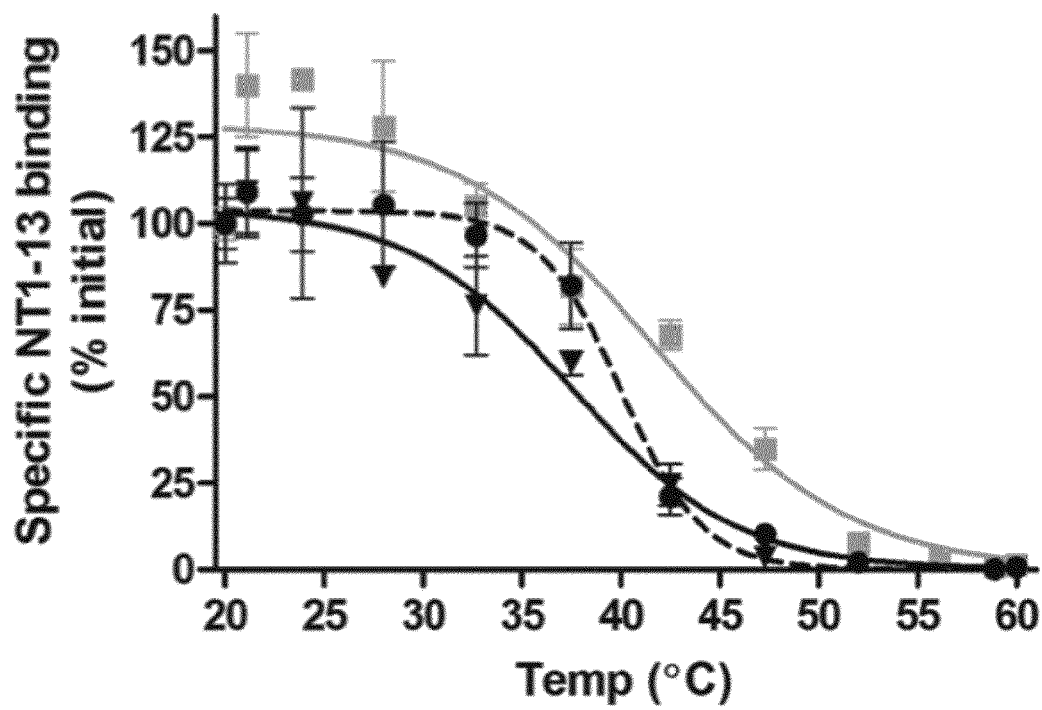
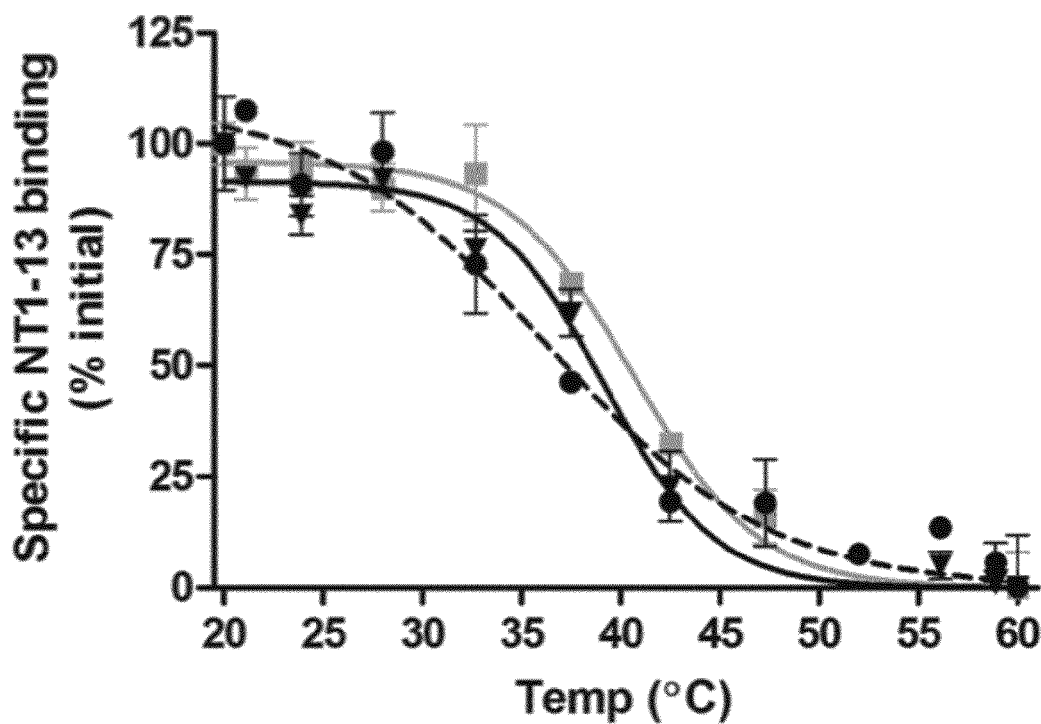

a b

CELLULAR HIGH THROUGHPUT ENCAPSULATION FOR SCREENING OR SELECTION

Directed evolution provides proteins with improved properties. Evolved proteins have been exploited as industrial enzymes, binding molecules and important research tools. The critical step in all directed evolution methods is the selection or screening of protein libraries for desired phenotypes. Selection techniques allow the examination of very large libraries by linking the phenotype of a protein to its genotype, allowing rapid identification of interesting variants. Selection methods such as phage display, yeast display, bacterial display, mRNA display and ribosome display are well established and routinely used to identify interesting biomolecules from large libraries, however none of these methods are suited to the selection of proteins that depend on complex intracellular synthesis or processing steps, or the presence of intracellular structures for their functional integrity. One example for a protein class that cannot be obtained by conventional means is the group of G-protein coupled receptors (GPCR). GPCR mutants that are stable in detergent micelles are an attractive target for research due to their importance in understanding GPCR structure and biochemistry.

Bacterial display uses the bacterial cell to physically contain a given protein and the plasmid that encodes it. Bacterial display has been applied to different GPCRs to acquire mutants with greatly improved functional expression in $E.$ $coli$. While many of these high expressing GPCRs are more stable in detergent, the correlation between high expression and high stability in detergent micelles is weak at best.

Abbreviations used herein are: GPCR (G protein-coupled receptor), NT (neurotensin peptide), FACS (fluorescence-activated cell sorting), DDM (n-Dodecyl-β-D-Maltopyranoside), DM (n-Decyl-β-D-Maltopyranoside), OG (n-Octyl-β-D-Glucopyranoside), LbL (Layer by Layer), CHAPS (3[(3-cholamidopropyl)-dimethylammonio]-1-propane sulfonate/N,N-dimethyl-3-sulfo-N[3-[[3α,5β,7α,12α)-3,7,12-trihydroxy-24-oxocholan-24-yl]amino]propyl]-1-propanaminium hydroxide); CHS (cholesteryl hemisuccinate Tris salt); CHESS (Cellular High throughput Encapsulation, Solubilization and Screening); HL-NT (Hi-Lyte Fluor 647 labelled neurotensin peptide (8-13)); FL-NT (BODIPY FL labelled neurotensin peptide (8-13)); FL-prazosin (BODIPY FL labelled prazosin).

The present invention provides a method for selecting a sequence set from a library of expressed nucleic acid sequences. It generally proceeds by the following steps:
- a plurality of cells is provided, wherein each of the cells comprises an expressed nucleic acid sequence, and this nucleic acid sequence is expressed in the cell and gives rise to a target protein,
- said plurality of cells is encapsulated in an encapsulating step, wherein cells are treated with a cationic polysaccharide ("cationic treatment step") and with an anionic polysaccharide ("anionic treatment step"), whereafter the cells are referred to as "encapsulated cells",
- the encapsulated cells are solubilized ("solubilization step") so that their membrane is disrupted to allow for the entry or departure of small molecules (low molecular mass compounds such as oligopeptides) into the cell or out of the cell, whereas the larger structures such as globular proteins are retained in the cell; the now encapsulated and solubilized cells are referred to as "solubilized compartments";
- the solubilized compartments are contacted with
  - a ligand to said target protein, wherein the ligand bears a detectable label, or
  - an indicator of an enzymatic activity of said target protein, and the enzymatic activity converts the indicator to a detectable label, ("labelling step");
- a subset of the solubilized compartments is selected as a function of the amount of detectable label present in each solubilized compartment ("selection step"), the selected solubilized compartments are referred to as "selection", and
- the expressed nucleic acid sequences are isolated from the selection as a selected sequence set ("isolation step").

One non-limiting example for a cationic polysaccharide is chitosan. Chitosan (CAS no. 9012-76-4) is a (random) linear polymer of β-1-4-D-glucosamine and N-acetyl-D-glucosamine.

One non-limiting example for an anionic polysaccharide is alginate; another is hyaluronic acid. Alginate (CAS no. 9005-32-7) is a linear copolymer of (1-4)-β-D-mannuronate and alpha-L-guluronate. Hyaluronic acid (CAS no. 9004-61-9) is a glycosaminoglycan. Other polyions for practicing the invention include, without being restricted to, poly-L-lysine, carboxymethylcellulose, poly(sodium 4-styrenesulfonate), poly(allylamine hydrochloride), sodium polystyrene sulfonate, poly(styrene)-co-styrene sodium sulfonate (NaPSS), PLGA (polylactic-co-glycolic acid), polyacrylic acid or a water soluble polycationic polymer known for use in the cosmetics industry such as one of the polyquaternium list of compounds (a designation for different polycationic polymers used in the cosmetic industry; see the Wikipedia entry for "polyquaternium").

In one embodiment, the cationic treatment step precedes the anionic treatment step. The initial layer depends on the properties of the template surface. For $E.$ $coli$, the surface of the cell is negatively charged due to the lipopolysaccharide (LPS) comprising the external face of the outer membrane. This makes the cell amenable to initial coating with a positively charged polymer. The process order can be reversed (i.e. the negatively charged layer is applied first) if a particular cell has a positively charged surface.

In one embodiment, the encapsulation step proceeds over several rounds, repeating the sequence of anionic and cationic coating. Thus, the cationic treatment step followed by an anionic treatment step may be repeated for example 2, 3, 4, 5, 6, 7, 8, 9 or 10 times, giving rise to ever thicker capsules.

The solubilization step disrupts the cell wall or outer membrane (and the inner membrane in the case of gram negative bacteria such as $E.$ $coli$) and exposes the cell's interior, whereas the coating applied to the cell during the encapsulation step retains larger structures in the cell to be probed in subsequent steps. The size limit can be tuned by adjusting the polyelectrolytes used (molecular weight) and the amount of layers deposited in the encapsulating step. This allows "tuning" of the method of the invention to allow for retention of a particular protein of interest; likewise it allows to provide for entry for a particular size of probe or ligand into the cell.

The solubilization step may employ any method that does not disrupt the polymer layers coated onto the cell during the encapsulation step. Examples include: detergent treatment perforin, lysozyme, mild ultrasonic treatment, hyper-osmotic or hypo-osmotic shock, electroporation, alcohol treatment, freeze-thaw cycles, heating and boiling the capsules and pressure gradients.

In some embodiments, solubilizing the membrane of said encapsulated cells in a solubilization step, giving rise to a plurality of solubilized compartments, comprises the step of exposing said plurality of encapsulated cells to a detergent in aqueous solution.

Thus, in some embodiments the method of the invention comprises providing a plurality of bacterial cells, each cell comprising an expressed nucleic acid sequence expressed as a target protein in each cell, encapsulating said plurality of cells in an encapsulating step, comprising treating said plurality of bacterial cells with a cationic polysaccharide in a cationic treatment step, treating said plurality of bacterial cells with an anionic polysaccharide in an anionic treatment step, said encapsulating step giving rise to a plurality of encapsulated bacterial cells, solubilizing the membrane of said encapsulated bacterial cells with a detergent in a solubilization step, giving rise to a plurality of solubilized compartments, contacting said plurality of solubilized compartments, in a labelling step, with a ligand to said target protein, said ligand bearing a detectable label, or with an indicator of an enzymatic activity of said target protein, said enzymatic activity converting said indicator to a detectable label, selecting a subset of said plurality of solubilized compartments as a function of detectable label present in said solubilized compartments in a selection step, giving rise to a selection, and isolating said expressed nucleic acid sequences from the selection as a selected sequence set in an isolation step.

In one embodiment, encapsulated *E. coli* cells expressing GPCRs localised to the inner cell membrane are treated for several hours with an aqueous solution of 2% n-decyl-β-D-maltopyranoside, a detergent that solubilizes the cell membranes. Receptor molecules are thus removed from the cell membrane and solubilized into n-decyl-β-D-maltopyranoside micelles inside the solubilized compartment. Other detergents such as DDM, OG, CHAPS and mixtures of any of these have also been used (see Examples).

According to one alternative of the labelling step, the solubilized compartments are contacted with a ligand to the target protein, and the ligand bears a detectable label. The ligand that is contacted with the solubilized compartments is able to enter the solubilized compartment through the perforation or holes in the cell wall or outer membrane—if any is left—and through the encapsulation coated onto the cell in the encapsulation step, to probe the target protein retained inside the solubilized compartment.

Non-limiting examples for a ligand to practice the invention are an oligopeptide, an (allosteric) enzyme agonist or antagonist or ion channel agonist or antagonist, receptor agonist or antagonist, inverse agonist, reverse agonist and allosteric modulator. The ligand may also be an enzyme substrate or a transition state analogue binding to a variant of the target protein. Other non-limiting examples for ligands are specific binding molecules such as antibodies, DARPins (see US20120142611 (A1), incorporated by reference herein), FABs, nanobodies or single chain variable fragments (scFv). Depending on the size of the pores of the solubilized membrane coating and the number of added polymer layers, also functional proteins (polypeptides) may be used as ligands.

According to another alternative of the labelling step, the solubilized compartments are contacted with an indicator of an enzymatic activity of the target protein. The enzymatic activity converts the indicator into a dye (which after conversion has a different absorption or fluorescence spectrum than the indicator prior to conversion) that serves as a detectable label, enabling the detection and further selection of the cell or compartment. Thus, according to this alternative the labelling step is ligand independent, e.g. a generic redox indicator can be used to detect the activity of peroxidases. By way of non-limiting example, the activity of fumarate reductase can be detected in a solubilized compartment in the presence of detergent. Cells expressing fumarate reductase or mutated fumarate reductase are encapsulated and the compartments solubilized with detergent. Water soluble 3-(4,5-dimethylthiazol-2-yl)-2,5-diphenyltetrazolium bromide (MTT) is then added to the solubilized compartments, where it enters the compartment and any active fumarate reductase reduces the MTT to insoluble, purple coloured formazan. The formazan precipitate remains inside the solubilized compartment and its presence in particular compartments can be detected and isolated using flow cytometry (FACS).

In one embodiment, the detectable label is a fluorescent dye. Non-limiting examples of fluorescent dyes are 4',6-diamidino-2-phenylindole, dihydrochloride (DAPI), xanthene dyes such as 5- or 6-Carboxyfluorescein (5-FAM and 6-FAM) or Fluorescein, rhodamine dyes such as 5- or 6-Carboxytetramethylrhodamine (5 or 6-TAMRA), or cyanine dyes.

The selection step may proceed by any method that allows for discrimination of the cells or compartments by the amount or quality of label therein. For fluorescent labels, FACS (fluorescence activated cell sorting) is the method of choice.

In one embodiment, the selected sequence set is submitted to another round of selection according to the method of the invention. The selected sequence set is thus subcloned and transfected into cells anew, and submitted to the sequence of encapsulation step, solubilization step, labelling step, selection step and isolation step, one or several times. The repetition may be applied to the selected sequence set of the previous repetition without further manipulation of the selected sequence set. In one embodiment, the selected sequence set is mutated, for example by error prone PCR (Chen & Arnold, Proc. Nat. Acad. Sci. USA 1993, 90:5618-5622). This method introduces point mutations, it alters the sequence in small steps without substantially altering the length of any individual sequence, adding "noise" to the selected sequence set to introduce mutations from which subsequent rounds of selection can choose. Alternatives or complements are DNA shuffling or saturation mutagenesis (Stemmer, Nature 1994, 370:389-391; Miyazaki & Arnold, J. Mol. Evol. 1999, 49: 716-720).

Alternatively, in one embodiment the selected sequence set is subjected to a treatment that deletes sequence tracts, recombines or shuffles sequence tracts between selected sequences, or introduces new sequence tracts randomly. Such manipulation is equivalent to recombination in a physiological setting and enables larger "leaps" in evolutionary space. In one embodiment, both point mutation and recombination are combined. Thus, the selected sequence set is diversified by amplification of said expressed nucleic acid sequences by a process introducing mutations into the amplified sequence, and/or by deletion or insertion of sequence tracts into said expressed nucleic acid sequences, and subsequently, the selected sequence set is submitted to another sequence of encapsulation step, solubilization step, labelling step, selection step and isolation step. Methods for introducing sequence variants are reviewed by Dalby (Curr. Opin. Struct. Biology 2011, 21, 473-480) and references cited therein.

The library of expressed nucleic acid sequences may be a random library or a library composed of homologous sequences, or sequences that are expressed in certain cells, tissues, pathological states, or in any other way connected to a parameter of interest. In one embodiment, the library of expressed nucleic acid sequences is composed of homologous sequences of 60%, 65%, 70%, 75%, 80%, 85%, 90%, 95% or more percent identity with each other.

Identity in the context of the present invention is a single quantitative parameter representing the result of a sequence comparison position by position. Methods of sequence comparison are known in the art; the BLAST algorithm available publicly is an example.

In most embodiments, the expressed nucleic acid sequence is part of a transgene expression construct present in the cell(s), for example an expression plasmid. In one embodiment, the expressed nucleic acid sequence is genomic and the plurality of cells is a population of mutants. In one embodiment, the plurality of cells is a heterologous mixture of cell types or organisms. This allows searching for rare phenotypes, for example hyper-stable enzymes in environmentally derived samples of organisms.

The target protein may be any protein expressed in the cell and retained in the solubilized compartment after encapsulation and solubilization. One important non-limiting example is a G-protein coupled receptor protein. Other non-limiting examples include ion channels, enzymes, nuclear receptors, transcription factors and DNA/RNA-binding proteins. Other examples for target proteins are specific binding molecules such as antibodies, DARPins, FABs, nanobodies or single chain variable fragments (scFv). Small-molecular weight target proteins are retained in the solubilized compartments by fusion to other oligopeptides or proteins to form larger structures (e.g. a triple GFP tag), or by reduction of the effective pore size of the solubilized compartment by an increased number of polymer layers.

In principle, any kind of cell (in the biological meaning of the word) can be used. The term cell in the context of the present specification thus includes (gram-positive and gram-negative) bacterial cells, eukaryotic cells including plant cells, mammalian cells including mammalian cell-culture adapted cells, or any other cell amenable to the steps of encapsulation and subsequent disruption of the cell's natural containment. The examples shown herein make use of bacterial cells; however the scope of the present invention is not limited to bacterial cells.

In one embodiment, the cells are bacterial cells. In one embodiment, the cells are isolated suspended mammalian cells in cell culture. In one embodiment, the cells are isolated suspended plant cells in cell culture.

In one embodiment, the detectable label is a fluorescent dye and said selection step is accomplished by fluorescent cell sorting.

In one embodiment, the cells are E. coli cells, the target protein is a G-protein coupled receptor and the detectable label is a fluorescent dye.

Wherever alternatives for single separable features such as, for example, a cell, a target protein, a cationic polysaccharide, an anionic polysaccharide, a detectable label or a selection protocol are laid out herein as "embodiments", it is to be understood that such alternatives may be combined freely to form discrete embodiments of the invention disclosed herein.

The invention is further illustrated by the following figures and examples, from which further embodiments and advantages can be derived:

SHORT DESCRIPTION OF THE FIGURES

Figure 1:
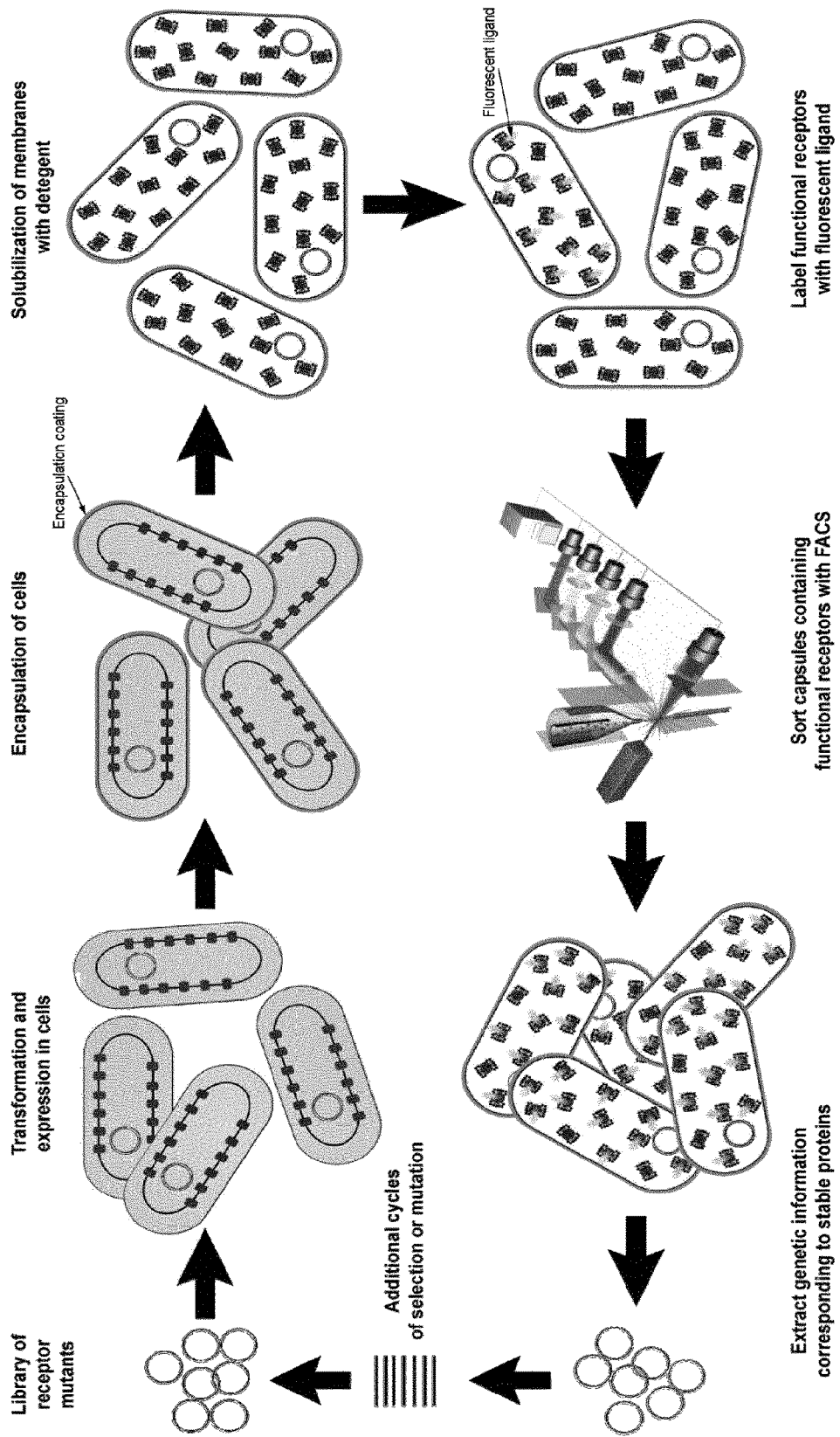

FIG. 1 shows a schematic representation of one embodiment of the invention. A library of receptor mutants is transformed and expressed in E. coli. Cells are encapsulated and the cell membrane permeabilized with detergent. The encapsulation layer serves as a semi-permeable barrier, retaining the solubilised receptor and its encoding plasmid within the capsule, but allowing fluorescently labelled ligand into the capsule where it can bind to functional receptor molecules. Capsules containing detergent stable GPCR mutants are more fluorescent and can be sorted from the population with FACS. Genetic material is recovered from the sorted capsules and used to either identify desired receptor mutants or as a template for further rounds of mutation or selection.

FIG. 2 shows a schematic representation of the LbL encapsulation of E. coli cells and the optimization of this method for the current invention (a) E. coli cells were encapsulated by laying down alternate layers of positively charged chitosan polymer and negatively charged alginate. (b) The amount of aggregated cells produced during the "Hillberg" LbL process was greatly reduced by the addition of EDTA (+EDTA) to the encapsulation solutions of alginate and chitosan. (c) Reducing the pH of the encapsulation solutions below 7 resulted in stronger capsules that were able to resist detergent treatment.

FIG. 3 shows the characterization of encapsulated cells. GPCR-expressing E. coli cells were encapsulated with 1 layer of chitosan and 1 layer of alginate in triplicate and analyzed with FACS. (a) The laser scattering properties of the naked cells allowed the definition of an arbitary gate enclosing 91.4% single cells. (b) 60.5% of particles detected in the encapsulated cell sample fell within this gate, with most of the remaining particles exhibiting scattering properties characteristic of larger particles. (c) Naked and encapsulated cells were exposed to detergent (1% DDM, 0.6% CHAPS, 0.12% CHS) and the loss of cell-like particles over time assayed with FACS. Detergent treatment of naked cells resulted in a rapid loss of cell-like particles (black open circles), whereas the detergent-treated encapsulated cell sample (grey open squares) maintained a high proportion of cell-like nanoparticles over the 15 day period. Untreated naked cells (black solid triangles) and untreated encapsulated cells (grey solid squares) both maintained a high proportion of cell-like particles over time. (d) C-terminally sfGFP-tagged D03- and C7E02-expressing cells were encapsulated and exposed to a mild detergent mixture (SAB) or harsh detergent (DM) in the presence of HL-NT. The sfGFP fluorescence contained within the capsules was measured using FACS for 15 days. No significant reduction in the mean fluorescence intensity (MFI) in the sfGFP channel was observed in the samples, indicating that the expressed receptors did not leak out of the nanocapsules. (e) Conversely, the average level of bound ligand per capsule varied more over the 15 day experiment. As expected, the activity of D03 in DM reduced over time. The fluorescence of the C7E02 samples tended to increase over the first 2 days before returning to the initial level after 15 days, indicating that this mutant was still able to bind ligand.

Figure 4:
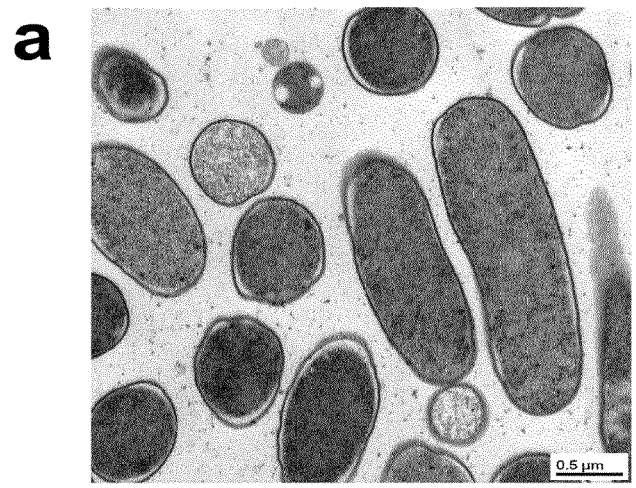
Figure 4:
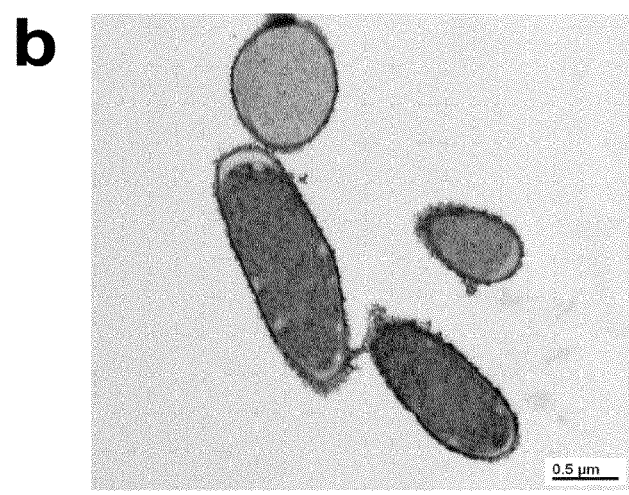
Figure 4:
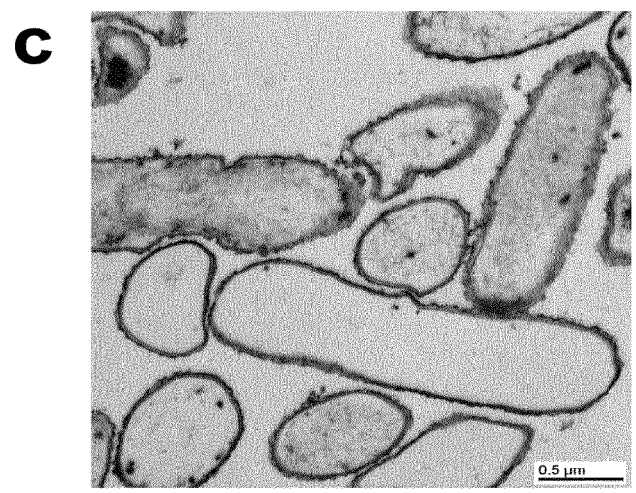

FIG. 4 shows electron micrograph images of encapsulated cells. (a) Naked *E. coli* cells, (b) encapsulated cells and (c) encapsulated cells treated with 1% DDM for 24 h were visualized with transmission electron microscopy.

FIG. 5 shows the selection of detergent stable 303 library members. Detergent stable "303 library" members were selected with FACS. (a) Fluorescence histograms of the sorted populations revealed strong enrichment of detergent stable receptors. (b) 22 selected clones were expressed individually, solubilized and assayed for ligand binding activity after 2 or 100 h in OG. The top 3 receptors were expressed and solubilized in 1.7% DM for 3 h at 20° C. Solubilized receptors were captured from the supernatant with streptavidin paramagnetic beads at 4° C. for 1 h. (c) C7E02 (grey circles), 303OGB5 (grey squares), 303OGG7 (black circles) or 303OGG8 (black triangles) coated beads were either treated with 20 nM HL-NT(8-13) in 1.7% DM for 1 h before being thermally challenged for 30 min at increasing temperatures or (d) treated with 20 nM HL-NT (8-13) after heating in the absence of ligand. (e) Alternatively, after solubilization in 1.7% DM, receptor coated beads were washed for 15 min in 2% OG at 4° C. without ligand before being either exposed to 20 nM HL-NT(8-13) in 2% OG for 1 h and then being thermally challenged for 30 min at increasing temperatures or (f) treated with 20 nM HL-NT(8-13) after heating in the absence of ligand. No specific signal could be measured from C7E02 coated beads in 2% OG. Parallel measurements were taken at every temperature point in the presence of 5 µM NT(8-13) as a competitor to determine the specific fluorescence signal. Data points are plotted as the mean of duplicate measurements, 100% represents the signal measured after heating at 20° C. for 30 min. Error bars indicate the standard error of the mean.

Figure 6:
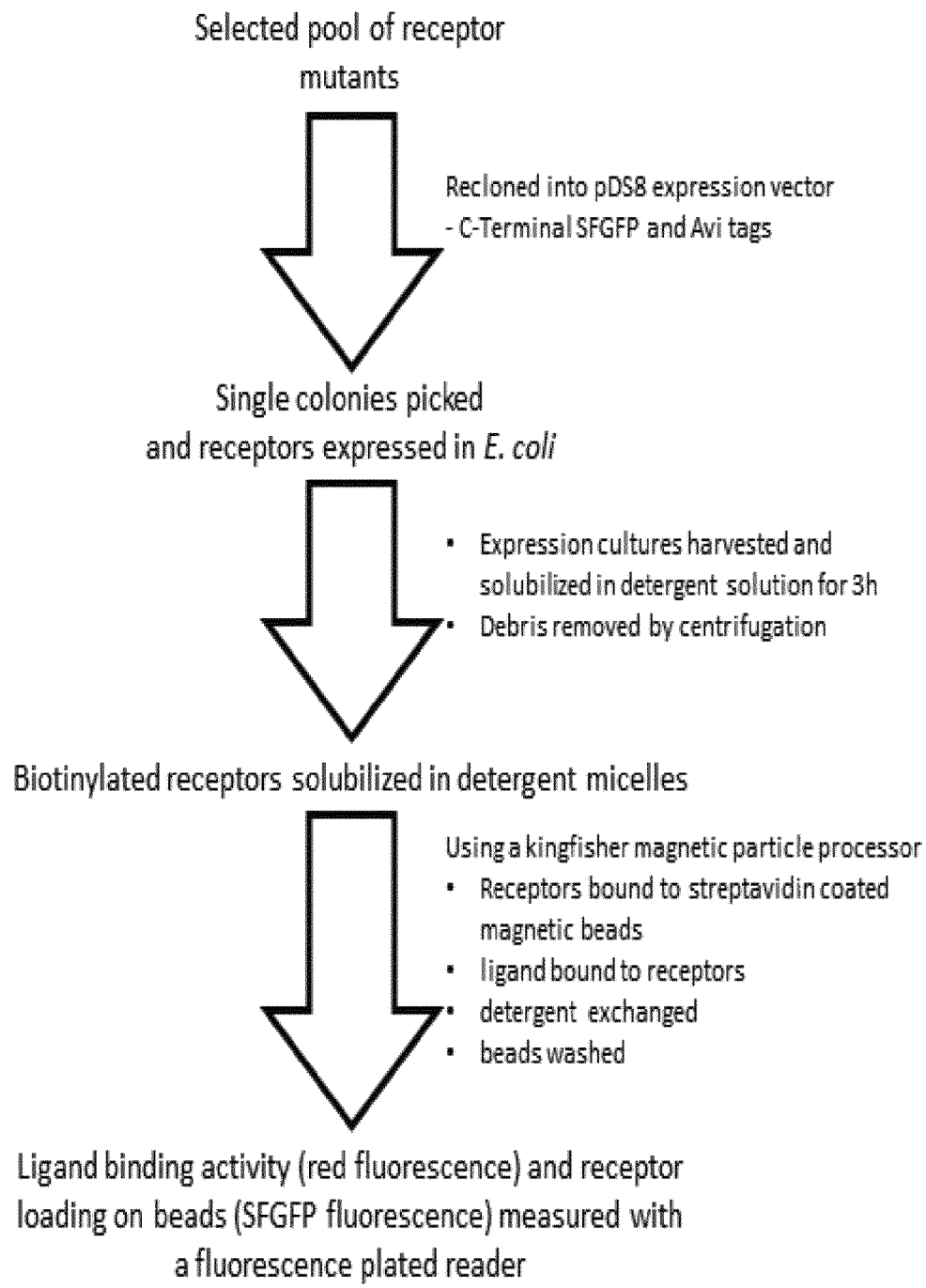

FIG. 6 shows the method used to characterize selected 303 library members.

Figure 7:
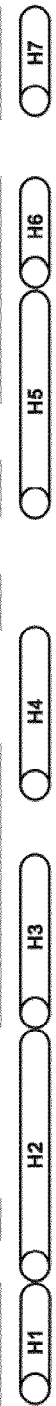

FIG. 7 shows the amino acid sequences of highly stable selected 303 library members. The amino acid sequences of the selected receptors were aligned with parental rat NTS1, D03 and the high expressing clone C7E02. Locations of the transmembrane helices are indicated with cylinders whereas the number of mutations over D03 are shown in the Δ column.

Figure 8:
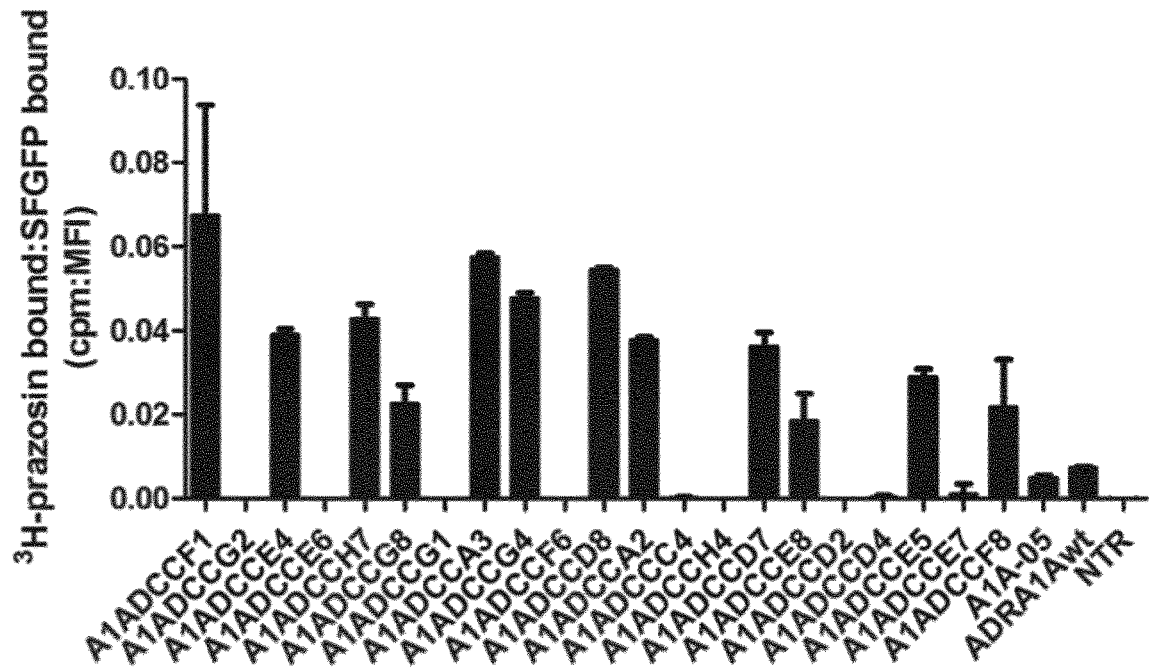
Figure 8:
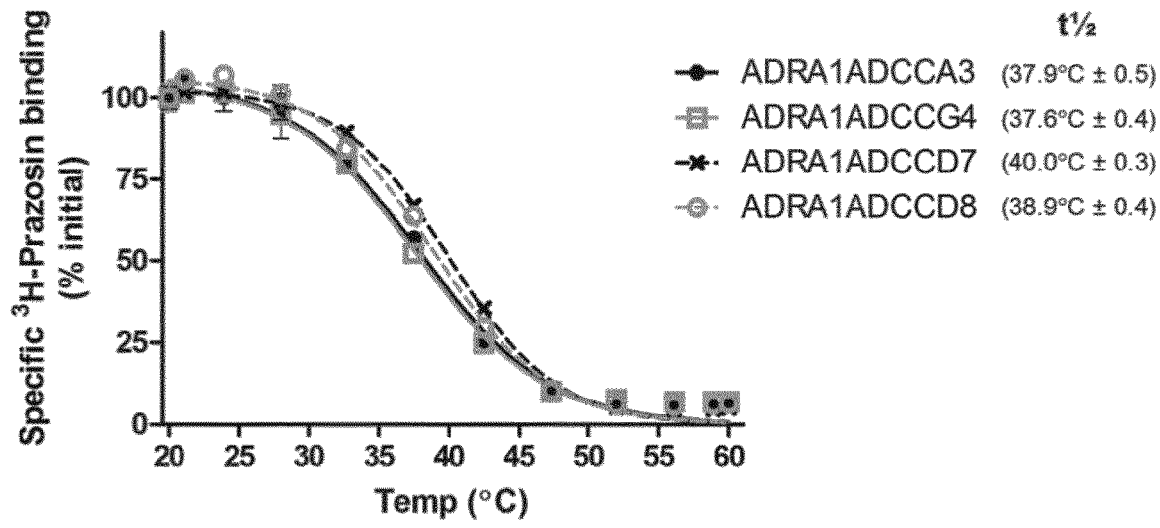
Figure 8:
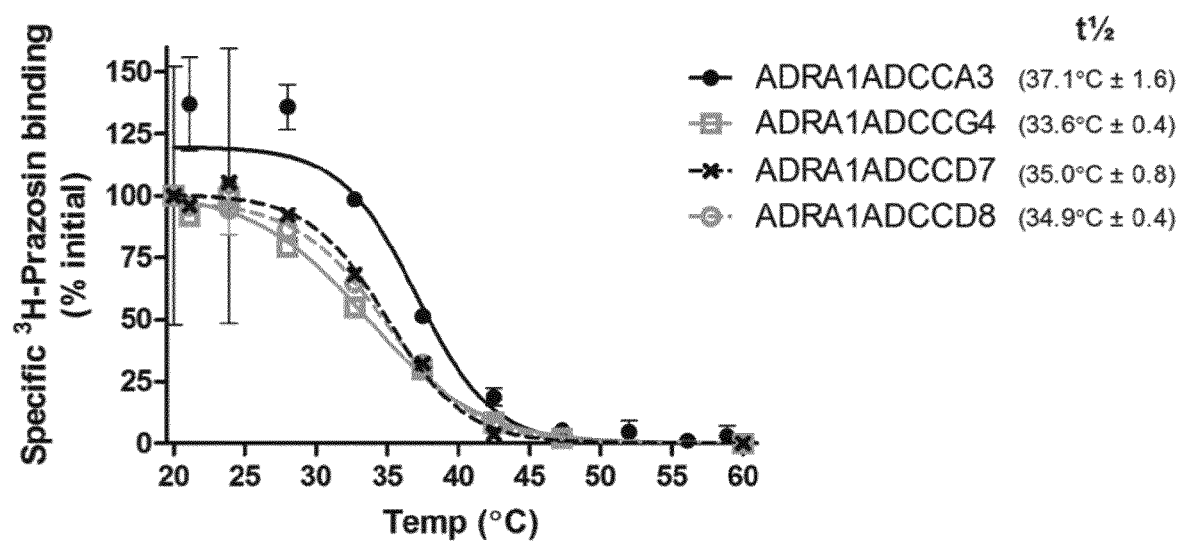

FIG. 8 shows the selection of detergent stable ADRA1A mutants with CHESS. Detergent-stable ADRA1A library members were selected with FACS using 200 nM BODIPY FL prazosin. (a) 21 selected clones were expressed individually, solubilized and assayed for ligand binding activity after 3 hours in PBS-E(DCC). (b) The top 4 receptors were solubilized in PBS-E(DCC) for 3 h at 20° C. in the absence of ligand. Solubilized receptors were captured from the supernatant with streptavidin paramagnetic beads at 4° C. for 1 h. ADRA1ADCCA3 (black circles), ADRA1ADCCG4 (grey open squares), ADRA1ADCCD7 (black crosses) or ADRA1ADCCD8 (grey open circles) coated beads were either treated with 20 nM [$^3$H]prazosin for 1 h before being thermally challenged for 30 min at increasing temperatures or (c) treated with 20 nM [$^3$H]prazosin after heating in the absence of ligand. No significant signal could be measured from ADRA1A- or A1A-05-coated beads when the receptors were solubilized in the absence of ligand. Parallel measurements were taken for every receptor in the presence of 10 µM unlabeled prasozin as a competitor to determine the specific fluorescence signal. Data points are plotted as the mean of duplicate measurements, 100% represents the signal measured after heating at 20° C. for 30 min. Error bars indicate the standard error of the mean.

Figure 9:

FIG. 9 shows the amino acid sequences of stable selected ADRA1A library members. The amino acid sequences of the selected receptors were aligned with parental ADRA1A and the previously identified high expressing mutant A1A-05. Locations of the transmembrane helices are indicated with cylinders whereas the number of mutations over ADRA1A are shown in the L column.

EXAMPLES

Selection of Detergent Stable G Protein-Coupled Receptors

G protein coupled receptors (GPCRs) are integral membrane proteins of considerable therapeutic interest. The GPCR gene family is the largest in the human genome and encodes approximately 850 different receptors that sense and respond to a huge variety of stimuli. For most biophysical and structural studies, receptors need to be first solubilized in detergents and purified. While the crystal structures of several GPCRs have been solved, frequently as a fusion with T4-lysozyme, which would preclude coupling with G proteins, many members of this family are too unstable for such studies.

The challenge for a wider study of this family is that no approach, either rational or evolutionary, has been described that would allow direct improvement of the detergent stability of integral membrane proteins. Stabilizing mutations have been previously identified using semi-rational trial and error or alanine scanning and screening approaches. However, even with automated platforms, only small numbers of mutants can be screened, since analysis must be performed on individually prepared lysates. Alternatively, a directed evolution method has been developed that selects for higher functional expression in bacteria (Sarkar et al., Proc Natl Acad Sci U S A, 2008. 105(39): p. 14808-13; Dodevski and Pluckthun, J Mol Biol, 2011. 408(4): p. 599-615). While higher functional expression in the membrane showed clear correlation with stability in mild detergents, resistance to short chain detergents might not directly correlate, since particular residues control the access of short-chain detergents to the protein interior, which cannot be accessed by bulky detergents or phospholipid molecules.

To nonetheless exploit the enormous powers of iterative directed evolution, we sought to carry out the receptor solubilization directly in a bacterial cell to allow the simultaneous screening of >10$^8$ cells, each expressing different receptor mutants, for GPCR variants that are detergent-soluble and functional. By using the cell as the primary compartment, we would maintain the connection of the GPCR phenotype to the genotype (the encoding plasmid) and thus use this screen as part of a Darwinian process, i.e. an iteration of selection and diversification.

The problem to be solved was that the cell would immediately disintegrate when exposed to detergent, thereby homogenizing the whole mixture of receptor mutants and plasmids, rendering the process useless for directed evolution, because the crucial genotype to phenotype linkage would be destroyed.

To solve this problem, our key concept was to encapsulate the cells. We envisaged that conversion of a GPCR-expressing (bacterial) cell into a detergent resistant nanocapsule, containing solubilized GPCR mutant proteins and the encoding plasmid, would permit the use of diverse libraries for molecular evolution of detergent-resistant GPCRs suitable for protein crystallization. The functional selection was adapted from selection of GPCRs to high functional expression in *E. coli* (Sarkar et al., ibid; Dodevski and Pluckthun, ibid.). A fluorescently labelled receptor ligand was applied to the cells, which bound to active receptor molecules. Bacterial cells expressing high amounts of active GPCR in the inner membrane, whose outer membrane is gently permeabilized, could then be selected using fluorescence-activated cell sorting (FACS) through multiple rounds of expression and selection. The genetic identity of the high expressing mutants could then be identified by sequencing the plasmids contained in the selected cells. In the present study, solubilized receptors need to be sorted, yet a similar FACS strategy could also be used with the encapsulated cells. The devised strategy was termed Cellular High throughput Encapsulation, Solubilization and Screening (CHESS) (FIG. 1).

Figure 2A:
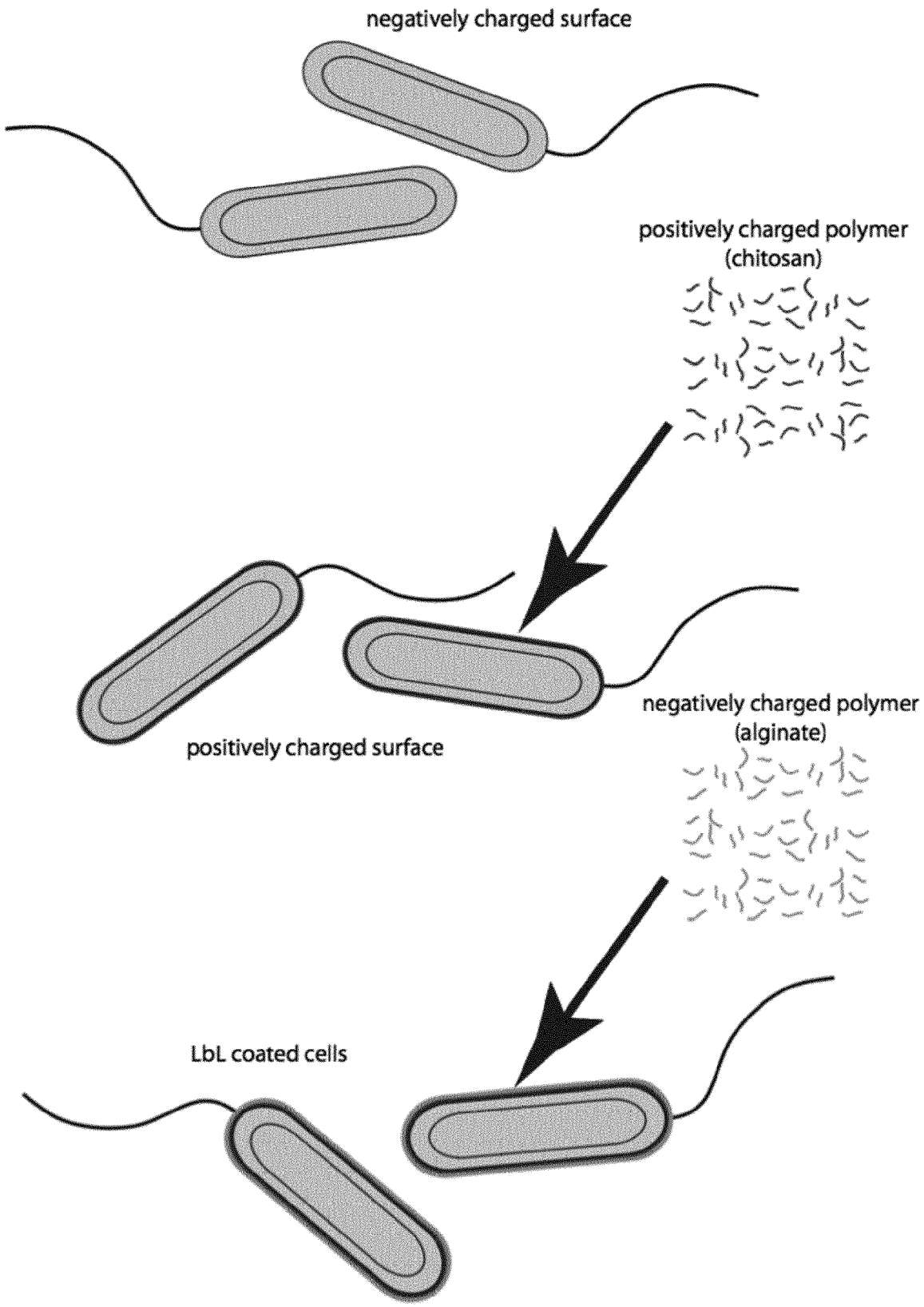

To encapsulate the cells we optimized a technology based on layer by layer (LbL) deposition of polyelectrolytes (Hillberg and Tabrizian, Biomacromolecules, 2006. 7(10): p. 2742-50). This method produced no empty capsules, few capsules containing multiple cells and could be easily scaled up to encapsulate large numbers of cells in batch (>$10^{10}$). The method utilized the negative surface charge of the *E. coli* cells contributed by the lipopolysaccharide displayed on the outer membrane, which aids in the deposition of a positively charged polymer, chitosan (poly-D-glucosamine), onto the cell. After washing away unbound chitosan, negatively charged alginate polymer was deposited, resulting in a strong coating of alternately charged, stable polymers (FIG. 2a). The encapsulation conditions were optimized by screening different buffers and pH values to maximize polymer deposition while minimizing cell aggregation (FIGS. 2b and 2c). The optimized conditions produced preparations consisting of mostly single-cell sized (FIGS. 3a and 3b), detergent-resistant (FIG. 3c) capsules when analyzed with flow cytometry and electron microscopy (FIG. 4). Encapsulation allowed detergent treatment of the whole cells, whose cell membrane disintegrated, while GPCR expressed in the inner membrane was solubilized in situ and retained within the capsule, even after exposure to detergent for 15 days (FIG. 3d).

Next we ensured that functional, detergent-solubilized GPCR molecules could be detected within the capsules and that stable GPCRs could be differentiated from unstable GPCR variants. For these experiments, two mutants of the rat neurotensin receptor (rNTS1) were utilized. D03 is a high expressing variant of rNTS1 that was identified using directed evolution with bacterial display and is stable in mild detergent. C7E02 is a variant derived from D03 that is very stable in DM micelles. We tested functionality by FACS: fluorescently labeled NTR1 ligand, HiLyte Fluor 647-labeled NT (HL-NT) could diffuse in through the capsule pores and be bound by the solubilized receptor. Using a mild detergent mixture (1% DDM, 0.5% CHAPS, 0.1% CHS and 30% glycerol), functional ligand binding of both solubilized receptors could be measured by FACS of the capsules over a period of 15 days (FIG. 3e). When treated with a harsher detergent buffer containing 1.7% DM, capsules containing D03 exhibited a loss of HL-NT binding within 10 h, whereas the stable receptor C7E02 exhibited ligand binding activity over the complete 15 day period (FIG. 3e). Interestingly, specific fluorescence signals measured from capsules containing stable receptors increased over time, probably due to clarification of the capsule by the detergents, resulting in less scattering of the fluorescence emission. Overall these experiments clearly demonstrated that we could probe the stability characteristics of different receptors that had been detergent-solubilized directly inside the nanocapsules.

To verify CHESS as a selection tool in directed evolution experiments, we applied the method to a previously established library known to contain some detergent-stable receptors. The "303 library" is a collection of rNTS1 mutants derived from D03. 30 variable positions in this library were identified from a saturation mutagenesis and high functional expression selection strategy. A further 3 amino acid substitutions were included in this library that have been reported to increase the stability of rNTS1. These 33 variable positions were recombined with wild-type residues to produce a library with a theoretical diversity of $8.6 \times 10^9$ individual mutants. This library was previously applied to bacterial display to identify high expressing mutants (see Schlinkmann et al., J. Mol. Biol. 2012, 422(3), 414-28). Several of these mutants, including C7E02, were discovered to be relatively stable in short chain detergents. Thus, this library could serve as a test case for CHESS selection, with the aim of direct isolation of receptors stable in short-chain detergents by screening the full library diversity.

Approximately $10^8$ transformants of *E. coli* DH5α containing GPCR library members were induced and allowed to express the GPCR, encapsulated and treated with 2% DM for 3 h at 20° C. without ligand, followed by 2 h at 20° C. in the presence of 20 nM FL-NT. In each round the top 0.5-1% of green fluorescent capsules were selected with FACS, followed by ultrasonic disruption of the capsules, PCR amplification, re-cloning and transformation of the selected mutants. In the second and third rounds, the short chain detergent octyl-glucoside (OG) was used for solubilization. The fluorescence intensity of the sorted populations from round 1 to 3 indicated strong enrichment of OG resistant rNTS1 variants in the sorted populations (FIG. 5a).

The mutants selected after the third round of sorting were cloned into an expression vector containing a C-terminal sfGFP fusion and an avi-tag for in vivo biotinylation [21]. To test their stability (FIG. 6), expressed receptor proteins were solubilized in 2% DM for 3 h at 20° C. and immobilized on streptavidin coated paramagnetic beads which allowed washing off of other proteins, and the detergent exchanged to 2% OG. HL-NT was added to bind to functional receptor molecules.

Of the 22 selected library members assayed, 20 exhibited significant ligand binding when solubilized in 2% OG for 2 h, whereas the parental gene, D03, was completely inactive (FIG. 5b). 13 clones exhibited significantly increased fractions of functional receptors over C7E02 after 2 h in 2% OG. After more than 4 days in 2% OG, 8 of these clones still displayed significant ligand binding, whereas C7E02 was completely inactive. It was encouraging that the application of CHESS to the "303 library" generated such a high frequency of OG resistant GPCRs.

The thermal denaturation profiles of the top 3 selected clones were measured in the presence or absence of ligand, when solubilized in 1.7% DM or 2% OG. 303OGB5, 303OGG7 and 303OGG8 exhibited enhanced thermal stability over C7E02 when heated in the presence or absence of NT in both DM and OG (FIG. 5c, d, e and f). Of particular note was the high stability of these receptors when heated in the absence of ligand, indicating a high degree of inherent receptor stability. In contrast, no activity could be measured for C7E02 under the same conditions, probably because C7E02 was not stable in OG without NT bound, and for these assays the detergent had been exchanged in the absence of ligand.

The clones selected through CHESS, 303OGB5, 303OGG7 and 303OGG8, on the other hand exhibited $T_{1/2}$ values of around 40° C. in OG in the presence or absence of ligand (FIG. 5e and f). The sequences of the receptors (FIG. 7) shows 22, 21 and 14 amino acid substitutions over D03, respectively, mainly located within the transmembrane helices.

To investigate whether CHESS could be generically applied to GPCRs, selection was applied to a library of the alpha 1A adrenergic receptor (ADRA1A), which had previously been subjected to two rounds of error-prone PCR and selection for high functional expression in *E. coli* (Dodevski and Pluckthun, ibid.). The encapsulated ADRA1A library was solubilized in situ by a detergent mixture (1% DDM, 0.5% CHAPS, 0.1% CHS, 30% glycerol) in the presence of BODIPY-FL-labelled prazosin (FL-prazosin) before FACS selection. After 3 sequential rounds of selection using the same detergent mixture, 21 single selected clones were assayed individually for increased stability in this detergent mixture (FIG. 8a). 12 of these receptors exhibited significantly higher stability than the wild-type ADRA1A and higher than the best mutant previously selected for high functional expression (A1A-05).

Thermal denaturation profiles of the top 4 selected clones were measured in the presence or absence of ligand (FIG. 8b and c). The top 4 selected clones, A1ADCCA3, A1ADCCG4, A1ADCCD7 and A1ADCCD8, exhibited $T_{1/2}$ values of around 40° C. in the presence of ligand, or around 35° C. in its absence. Under these conditions wild-type ADRA1A and the mutant A1A-05, selected for higher functional expression, appeared unstable in this detergent in the absence of ligand, even at 20° C., as no significant fluorescence signal was obtained. The receptors directly evolved for stability in detergent were found to contain between 12 and 14 amino acid substitutions compared to the wild type receptor (FIG. 9). Most of the mutations were localized within the 7 trans-membrane core of the receptor, mainly in helices 2, 3, 4 and 7, and many conserved substitutions were also found to be in the C-terminal tail of the receptor. Interestingly, all of the selected clones contained substitutions that were not identified in ADRA1A mutants selected from the same library for high functional expression (Dodevski and Pluckthun, ibid.), suggesting that CHESS enables the enrichment of low frequency mutations that specifically improve receptor stability in detergent. As with the selections of the NTS1 based library, CHESS was able to deliver the most detergent-stable ADRA1A isoforms reported to date.

The successful application of CHESS to two unrelated GPCRs indicates that CHESS is a novel, rapid method for directly generating GPCRs stable to harsh detergents that are perfectly suited to biophysical analyses and crystallography screens. By evolving receptors that are not dependent on fusion of T4 lysozyme into one of the loops the study of complexes with G-proteins is simplified. CHESS might allow the direct selection of receptor mutants favoring the binding of G-protein mimetics such as peptides or even the G-proteins themselves, which could potentiate the direct selection of receptors stabilized in active conformations.

Because the permeability of the capsules can be tuned by adding additional polyelectrolyte layers, CHESS may be applied to non-GPCR membrane proteins or soluble proteins such as enzymes. While it is a method to form microscopic compartments and thus similar in this respect to water-in-oil emulsions, it provides access to small molecules from and to the bulk solution, and each compartment is created directly from a bacterial cell. An application such as the one described, in which detergent is utilized, cannot be carried out with water-in-oil emulsions. All assays which would normally require cell disruption, such as membrane protein solubilization and stability testing, or enzymatic assays with cell-impermeable fluorogenic substrates, could now be carried out directly in these compartments created from live bacterial cells.

CHESS is suited to long term stability studies because, once properly encapsulated, CHESS capsules are stable for weeks. By directly converting a bacterial cell into a semipermeable stable capsule, the number of samples that can simultaneously be tested, compared to individual cell lysates, is probably increased by 5 or 6 orders of magnitude. In the field of membrane protein study, it is hoped that CHESS can become part of a generic solution to the difficulties associated with the direct evolution of proteins stable to harsh detergents, such as the GPCRs described here, in turn leading to a more complete understanding of these therapeutically relevant proteins.

MATERIALS AND METHODS

Plasmids, Receptor Libraries and Bacterial Expression

The *Escherichia coli* strain DH5α was used for all cloning and expression in this study. It was transformed with GPCR encoding plasmids or libraries and the proteins expressed as described previously (Sarkar et al., ibid.: Dodevski and Pluckthun, ibid.).

Encapsulation of Cells

For LbL encapsulation the protocol described by Hillberg et al. (ibid.) was followed with the following modifications; cells were harvested after protein expression by centrifuging at 3800 rcf in a swinging bucket centrifuge and washed 3 times with PBS pH 7.4, 1 mM EDTA and 25 µg/ml chloramphenicol (PBS-E). Cells were resuspended in PBS-E pH 6.0 containing 0.25 mg/ml low molecular weight chitosan (Sigma Aldrich) and mixed vigorously. Cells were collected by centrifuging at 1700 rcf in a swinging bucket centrifuge and washed 3 times with PBS-E pH 6.0 before being resuspended in PBS-E pH 6.0 containing 0.25 mg/ml low viscosity alginic acid (Sigma Aldrich) and subjected vigorous shaking. Capsules were washed 3 times in PBS-E pH 6.0 and finally resuspended in PBS-E pH 7.4. The particulate and fluorescent properties of encapsulated samples were characterized using a Partec CyFlow Space cytometer with volumetric particle counting capability. In ligand binding assays measured with FACS bacterial cells were exposed to 20 nM HiLyte Fluor 647 labelled NT(8-13) (HL-NT) (synthesized by Anaspec) for at least 2 h before being centrifuged and washed once before FACS analysis.

Transmission Electron Microscopy

An untreated *E. coli* culture was centrifuged in Eppendorf tubes and the supernatant was discarded. Cells from the pellet were drawn into cellulose capillary tubes and immediately immersed in 1-hexadecene to prevent drying. Tubes of about 4 mm length were cut using a scalpel and transferred into the 150 µm well of a 6 mm aluminium specimen carrier. Treated *E. coli* cultures were centrifuged in sealed 200 µl pipette tips. Supernatant was removed with filter paper, the sealed tip cut off and the pellet directly pipetted into the 100 µm cavity of a 6 mm aluminium specimen carrier. Samples were sandwiched with a flat 6 mm aluminium specimen carrier dipped in 1-hexadecene and high-pressure frozen with an EM HPM100 high-pressure freezer (Leica Microsystems, Vienna, Austria). The samples were freeze-substituted with anhydrous acetone containing 2% OsO$_4$ in an AFS2 freeze-substitution unit (Leica Microsystems). Samples were substituted for 8 h at −90° C., 8 h at −60° C., 8 h at −30° C., and 1 h at 0° C. with periodic temperature transition gradients of 30° C./h. Samples were then washed twice with anhydrous acetone at 4° C. and embedded in Epon/Araldite. Sections were post-stained with uranyl acetate and lead citrate and imaged in a Phillips CM 12 transmission electron microscope (FEI, Eindhoven, Netherlands) using a Gatan CCD camera (1 k×1 k) and digital micrograph acquisition software (Gatan GmbH, Munich, Germany).

Selection of Detergent Stable GPCRs From Libraries

E. coli cultures transformed with GPCR libraries were encapsulated and treated with PBS-E pH 7.4 containing complete protease inhibitors (Roche), 25 µg/ml chloramphenicol and 2% DM (PBS-E(DM)). For selections with the "303 library", the initial selection round involved challenging the encapsulated naïve library with 2% DM for 3 h at 20° C. with vigorous shaking without ligand, followed by 2 h at 20° C. in the presence of 20 nM BODIPY FL labelled NT(8-13) (FL-NT) (Sarkar et al.; ibid.). Capsules were washed twice in PBS-E(DM) solution before FACS selection of the top 0.5-1% fluorescent capsules in the FITC channel. Genetic information was recovered from the sorted capsules by PCR amplification using specific primers after ultrasonic disruption of the capsules in an ultrasonic water bath for 5 minutes. In the second and third rounds of selection, the capsules were solubilized in PBS-E(DM) as in the first round for 3 h, followed by addition of 20 nM FL-NT for 1 h, before the capsules were collected by centrifugation and resuspended in PBS-E containing 2% OG (PBS-E(OG)) and 20 nM FL-NT. Capsules were washed once in 20 nM FL-NT in PBS-E(OG) to promote efficient detergent exchange before being incubated for 2 h in 2% OG with ligand. Capsules were washed twice in PBS-E(OG) and the top 0.5-1% of the fluorescent capsules sorted with FACS.

For ADRA1A library selections, 3 rounds of selection were undertaken with identical conditions for every round. Capsules were solubilized with 1% DDM, 0.5% CHAPS, 0.1% in PBS, 1 mM EDTA, 30% glycerol at pH 7.4 containing 200 nM BODIPY-FL-prazosin (Invitrogen) (FL-prazosin). Capsules were washed twice in 1% DDM, 0.5% CHAPS, 0.1% CHS in PBS, 1 mM EDTA, 30% glycerol at pH 7.4 and the top 0.5-1% of the fluorescent capsules sorted with FACS.

Screening Selected Clones for Detergent Stability

PCR fragments amplified from the final rounds of selection were cloned into a vector containing a C-terminal sfGFP-AviTag fusion. Expression of GPCRs with a C-terminal Avi-tag has been previously shown to produce a high percentage of in vivo biotinylated receptor (Dodevski and Pluckthun, ibid.). Receptors were expressed in 24 deep-well plates and the cells solubilized in PBS-E(DM) containing 50 mg/ml chicken lysozyme (Sigma Aldrich). Plates were subjected to 5 min of sonication in an ultrasonic water bath before incubation for 3 h at 20° C. with vigorous shaking. Cell debris was removed with centrifugation and the supernatant containing solubilized receptor incubated with streptavidin coated paramagnetic beads (Invitrogen) and in the case of "303 library" members, 20 nM HL-NT for 1 h at 4° C. Solutions were mixed and the beads manipulated in 96 deep well plates with a kingfisher FLEX magnetic particle processor (Thermo scientific). For "303 library" members, receptor coated beads were transferred into 2 subsequent detergent exchange solutions of PBS-E(OG) containing 20 nM HL-NT. After 2 h or 100 h exposure to OG, beads were washed once in PBS-E(OG), before being transferred to clear bottom, black 96-well microplates (Greiner) in 100 µl PBS-E(OG) per well. HL-NT and sfGFP fluorescence levels were measured in each well using an M1000 dual monochromator fluorescence plate reader (Tecan), with excitation at 630 nm for HL-NT and 488 nm for sfGFP. The fluorescence emission signal at 668 nm was measured for HL-NT and 512 nm for sfGFP.

For single ADRA1A clone analysis the unavailability of a red fluorescently labelled ligand meant that we needed to use $^3$H-labelled prazosin (Invitrogen) for quantitating ligand binding to solubilized receptor. Expression and solubilization was carried out as above using the milder detergent mixture of PBS-E pH 7.4 containing 1% DDM, 0.5% CHAPS, 0.1% CHS and 30% glycerol (PBS-E(DCC)) further supplemented with 50 mg/ml chicken lysozyme and 20 nM [$^3$H]prazosin at 20° C. After binding to magnetic beads and washing, ¾ of the final bead solution per data point (15 µl) was resuspended in 200 µl of OptiPhase Supermix cocktail (PerkinElmer) and the $^3$H counts measured on a liquid scintillation counter (1450 Microbeta plus; PerkinElmer). The remaining ¼ of bead solution was resuspended in 100 µl PBS-E(DCC) in and the sfGFP fluorescence of each sample measured as above.

Thermostability Assays

NTS1 related receptors were expressed in 200 ml cultures for 20-24 h at 20° C. Cells were harvested with centrifugation, washed once with PBS-E and the cells disrupted with sonication (Sonifier 250, Branson). Lysed cells were collected with centrifugation and the supernatant discarded. The pellet was solubilized in PBS-E(DM) containing 50 mg/ml chicken lysozyme at 20° C. with vigorous shaking for 3 h. Insoluble material was removed by centrifugation and the supernatant exposed to streptavidin coated paramagnetic beads. Solubilized receptor was allowed to bind to the beads for 1 h at 4° C. before being transferred to new vessels containing either PBS-E(DM) or PBS-E(OG) without ligand and mixed for 15 min. Beads were resuspended into new vessels containing either PBS-E(DM) or PBS-E(OG), with or without ligand (or competitor). Bead containing solutions were distributed along rows of 96-well PCR plates and subjected to 30 min of heat treatment using a gradient PCR cycler (Biometra). Ligands were incubated with receptor-coated beads for 1.5 h before or after heating. Beads were washed once in the relevant detergent solution before being resuspended in clear bottom, black 96-well microplates and the residual fluorescence intensities of each well measures as above. Apparent T½ values were defined using non-linear regression fitting of the data with GraphPad Prism.

For ADRA1A derived clones, expression and sonication was conducted as above, but the pellet was solubilized in PBS-E(DCC) containing 50 mg/ml chicken lysozyme at 20° C. with vigorous shaking for 3 h in the absence of ligand. Heat and ligand treatment was performed as above, with the radioligand binding assay and curve fitting performed as described previously (Dodevski and Pluckthun, ibid.).

The invention claimed is:

1. A method for selecting a sequence set from a library of expressed nucleic acid sequences, comprising:
   providing a plurality of cells, each cell comprising an expressed nucleic acid sequence expressed as a membrane protein in said cell,
   encapsulating said plurality of cells in a single encapsulation step, comprising:
   treating said plurality of cells with a cationic polysaccharide in a cationic treatment step, and
   treating said plurality of cells with an anionic polysaccharide in an anionic treatment step,
   wherein said encapsulating step gives rise to a plurality of encapsulated cells which each have a detergent resistant coating, and wherein each encapsulated cell comprises an expressed nucleic acid sequence expressed as the membrane protein, solubilizing after the single encapsulation step a membrane of said plurality of encapsulated cells with a detergent to form a plurality of solubilized compartments that retain detergent solubilized membrane protein, wherein the detergent resistant coating comprises pores that retain the detergent solubilized membrane protein, and wherein the nucleic acid sequence is not expressed in each of the plurality of solubilized compartments, labeling said plurality of solubilized compartments by contacting said plurality of solubilized compartments, in a labeling step, with a ligand that binds to said membrane protein, said ligand bearing a detectable label, or with an indicator of an enzymatic activity of said membrane protein, said enzymatic activity converting said indicator to a detectable label, wherein said labeling step gives rise to plurality of labeled solubilized compartments, selecting a subset of said plurality of labeled solubilized compartments as a function of detectable label present in said labeled solubilized compartments, and isolating said expressed nucleic acid sequences from the subset as a selected sequence set.

2. The method according to claim 1, wherein the cationic polysaccharide is chitosan.

3. The method according to claim 1, wherein the anionic polysaccharide is alginate or hyaluronic acid.

4. The method according to claim 1, wherein the cationic treatment step precedes the anionic treatment step.

5. The method according to claim 1, wherein a sequence of steps comprising a cationic treatment step followed by an anionic treatment step is repeated two to ten times.

6. The method according to claim 1, wherein the detectable label is a fluorescent dye.

7. The method according to claim 1, wherein said ligand is an oligopeptide, agonist, antagonist, substrate or transition state analogue binding to a variant of said membrane protein.

8. The method according to claim 1, wherein the selected sequence set is transferred into a plurality of cells and submitted to a sequence of encapsulation step, solubilization step, labelling step, selection step and isolation step.

9. The method according to claim 1, wherein after said isolation step, said selected sequence set is diversified by a. amplification of said expressed nucleic acid sequences by a process introducing mutations into the amplified sequence, and/or by b. deletion or insertion of sequence tracts into said expressed nucleic acid sequences, and subsequently, the selected sequence set is submitted to another sequence of encapsulation step, solubilization step, labelling step, selection step and isolation step.

10. The method according to claim 1, wherein said library of expressed nucleic acid sequences is a library of homologous sequences of at least 60% identity with each other.

11. The method according to claim 1, wherein said expressed nucleic acid sequence is comprised in a transgene expression construct.

12. The method according to claim 11, wherein said transgene expression construct is plasmid.

13. The method according to claim 1, wherein said membrane protein is a G-protein coupled receptor protein, an ion channel, or an enzyme.

14. The method according to claim 1, wherein said cells are bacterial cells.

15. The method according to claim 1, wherein said detectable label is a fluorescent dye and said selection step is accomplished by fluorescent cell sorting.

* * * * *